United States Patent [19]

Stinson et al.

[11] Patent Number: 5,066,597

[45] Date of Patent: Nov. 19, 1991

[54] APPARATUS FOR INFECTIOUS RADIOACTIVE WASTE

[75] Inventors: Margaret C. Stinson, N. Billerica; Mitchell S. Galanek, Plymouth, both of Mass.

[73] Assignee: Massachusetts Institute of Technology, Cambridge, Mass.

[21] Appl. No.: 335,836

[22] Filed: Apr. 10, 1989

[51] Int. Cl.[5] .............................................. C12M 1/12

[52] U.S. Cl. ................................ 435/311; 250/506.1; 250/507.1; 252/626; 252/633; 220/371; 220/373; 220/87.1; 206/439; 206/484.1; 422/159; 422/184; 422/292; 422/294; 383/111; 383/113; 55/387

[58] Field of Search .................. 252/626, 633; 422/26, 422/119, 184, 292, 294, 295, 159; 206/439, 484.1; 220/87, 371, 373; 250/506.1, 507.1; 383/111, 113; 55/387, 385.1, 385.2, 385.4, D9; 435/35, 807, 311

[56] References Cited

U.S. PATENT DOCUMENTS

| | | | |
|---|---|---|---|
| 3,073,507 | 4/1960 | Trewella et al. | 206/439 |
| 3,092,249 | 3/1961 | Chapman | 206/439 |
| 3,229,813 | 1/1966 | Crowe, Jr et al. | 206/439 |
| 4,459,936 | 7/1984 | Karle | 422/26 |
| 4,592,192 | 6/1986 | Jacob et al. | 53/512 |
| 4,644,586 | 2/1987 | Padgett | 383/102 |
| 4,670,398 | 6/1987 | Song | 435/298 |
| 4,695,454 | 9/1987 | Prince et al. | 424/89 |
| 4,737,315 | 4/1988 | Suzuki et al. | 252/632 |
| 4,756,852 | 7/1988 | Temus | 252/633 |
| 4,849,184 | 7/1989 | Fougeron et al. | 422/159 |
| 4,935,371 | 6/1990 | Rickloff | 435/296 |

FOREIGN PATENT DOCUMENTS 236071 4/1960 Australia .

*Primary Examiner*—Edward A. Miller
*Assistant Examiner*—Ngoclan T. Mai
*Attorney, Agent, or Firm*—Thomas J. Engellenner; William C. Geary III

[57] ABSTRACT

An apparatus is disclosed for housing radioactively and biologically contaminated waste materials during treatment thereof to inactivate the biological contaminants and render the wastes more suitable for disposal in a solid landfill. The apparatus is nonporous and thermally resistant. Additionally, the apparatus features at least one opening within which is disposed a filter for entrapping any radioactive compounds contained in gases exiting the apparatus during the treatment. The apparatus is used in conjunction with an autoclaving procedure which inactivates the biological contaminants while preventing volatile radioactive compounds from escaping into the environment.

9 Claims, 2 Drawing Sheets

APPARATUS FOR INFECTIOUS RADIOACTIVE WASTE

BACKGROUND OF THE INVENTION

The present invention relates to the treatment of biologically and radioactively contaminated solid wastes prior to disposal. More particularly, the invention relates to a method and apparatus to facilitate autoclaving of such wastes to render them biologically harmless.

Recently, a great deal of biological and medical research has been directed to infectious diseases such as AIDS. In the course of such research it is common to use radioactive materials for such techniques as end-labelling of DNA, metabolic labelling of proteins, reverse transcriptase assays, Cr-release assays and cytotoxic T-lymphocyte assays. As a result, glassware, gloves and other solid laboratory materials often become contaminated with biological materials (e.g., viruses and bacteria) as well as with radioactive isotopes. Because these materials are biologically contaminated, they cannot be accepted at waste sites designated for disposal of radioactive materials. Also, conventional methods of inactivating biologically contaminated wastes (e.g., incineration and autoclaving) are not appropriate, due to the production of volatile radioactive compounds. This presents a disposal dilemma for solid materials which are both biologically and radioactively contaminated.

There is thus a need for safe, effective techniques for treating and/or disposing of solid waste materials which are both biologically and radioactively contaminated. Current practices for treating and handling materials which are either biologically or radioactively contaminated are not applicable to materials which are both biologically and radioactively contaminated.

It is therefore an object of the present invention to provide methods and apparatuses for treating and disposing of solid waste materials which are biologically and radioactively contaminated. A further object of the invention is to provide a method and apparatus to facilitate autoclaving of solid biologically and radioactively contaminated wastes in such a way that volatile radioactive compounds are not released into the environment and biological contaminants are inactivated. Additional objects will be apparent to those of ordinary skill in the art upon reading the following disclosure.

SUMMARY OF THE INVENTION

Method and apparatuses have been devised to enable radioactive and biological solid waste material to be treated by steam autoclaving in such a way that the biological waste is inactivated and radioactive gas does not escape into the environment during the autoclaving procedure. Following this treatment the waste material may be disposed of in a manner typical of any radioactive solid waste, such as in a licensed radioactive solid waste landfill.

In one embodiment, the apparatus consists of a specially adapted container and filter apparatus for housing the solid waste material during the autoclaving procedure. Preferably, the container is constructed of a transparent material which is nonporous. Additionally, the container has at least one opening into which a filter may be inserted. The filter functions to entrap radioactive compounds which may be contained within gases exiting the container during the autoclaving procedure. The filter is disposed within the opening of the container such that gas may exit the container only by passage through the filter. In order to ensure steam penetration of the waste, and to inactivate any biological materials, a small amount of an aqueous solution, such as water or other source of moisture, is placed within the container to generate steam during the autoclaving procedure.

When water is added to the container, an absorbent material should likewise be added to the container to absorb moisture within the container. It is undesirable to add excess water to the container as this may result in moisture remaining within the container.

In addition, heat sensitive controls, such as Diack tubes and/or autoclave tape, should be disposed both inside and outside of the container as indicators of a sufficient autoclaving protocol. Such heat sensitive controls, which are well known in the art, undergo a pronounced and visually apparent color change after exposure to sufficiently high temperatures.

Filter elements useful in the present invention can be of virtually any size, shape and construction sufficient to entrap any radioactive material contained in a gas exiting the container. Preferably, the filter has a flow path within which is disposed an absorbent material such as activated charcoal. Further filtration and entrapment of larger particulates may result when glass wool is used in conjunction with the activated charcoal.

BRIEF DESCRIPTION OF THE DRAWINGS

FIG. 2 is a perspective view, partially cut away, of a filter cartridge useful with the containment apparatus of FIG. 1.

FIG. 4 is a side perspective view, partially cut away, of a filter cartridge useful with the containment apparatus of FIG. 3.

DETAILED DESCRIPTION OF THE DRAWINGS

The present invention provides an apparatus 10 which enables radioactive and biologically contaminated materials to be autoclaved without a release into the environment of volatile radioactive materials.

Figure 1:
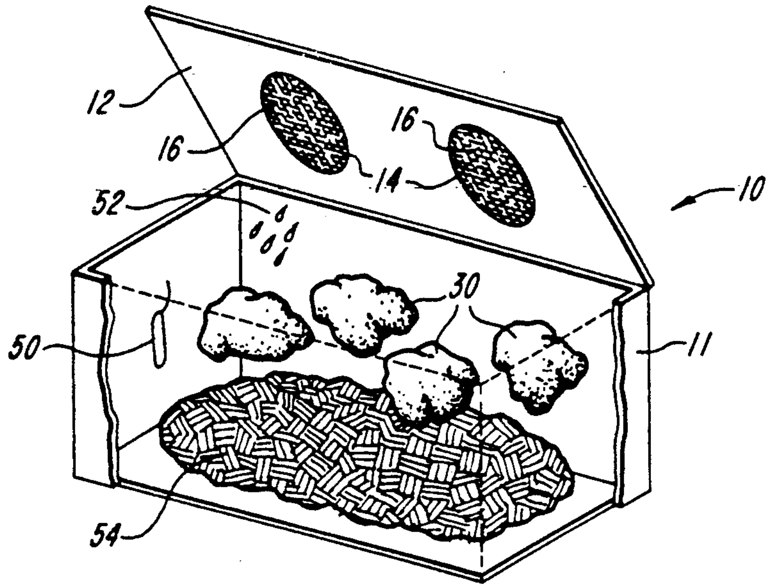
FIG. 1 is a perspective view of a containment apparatus according to the present invention.
Figure 3:
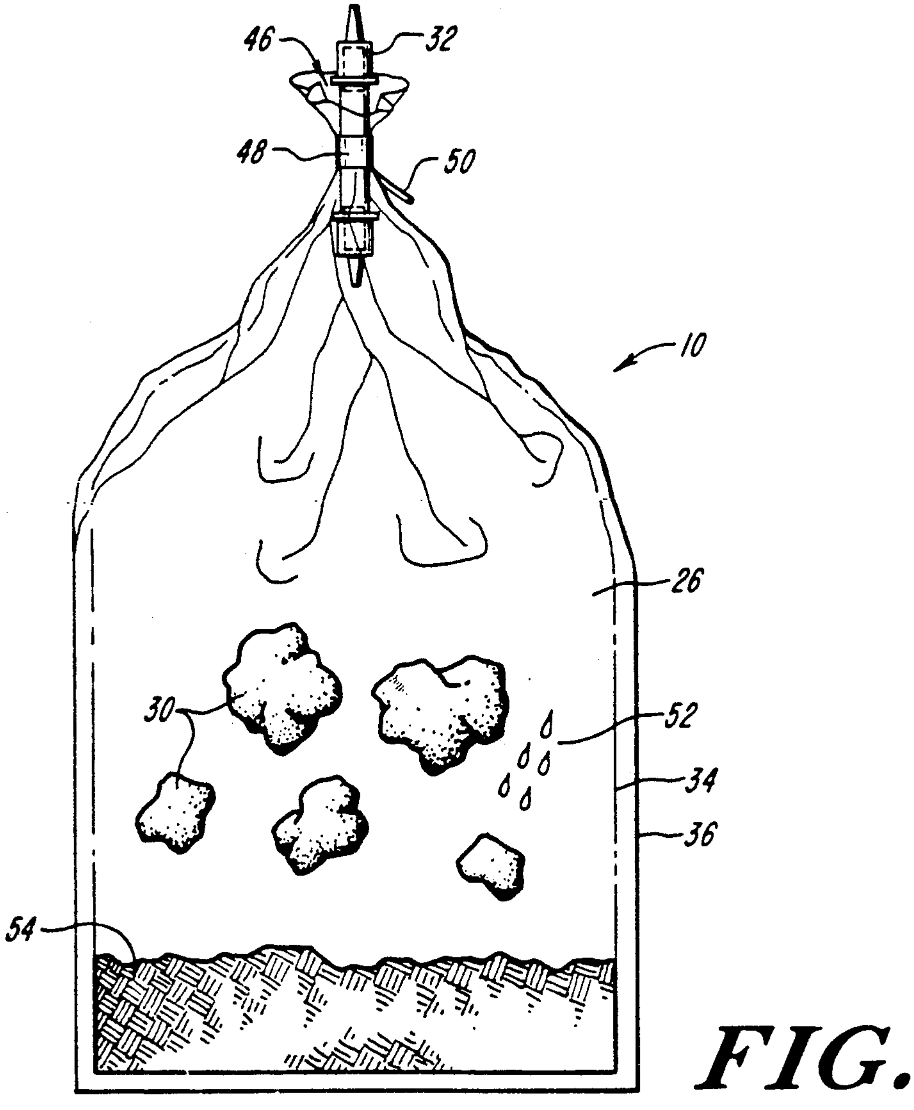
FIG. 3 is a perspective view of another containment apparatus according to the present invention.
Figure 1:
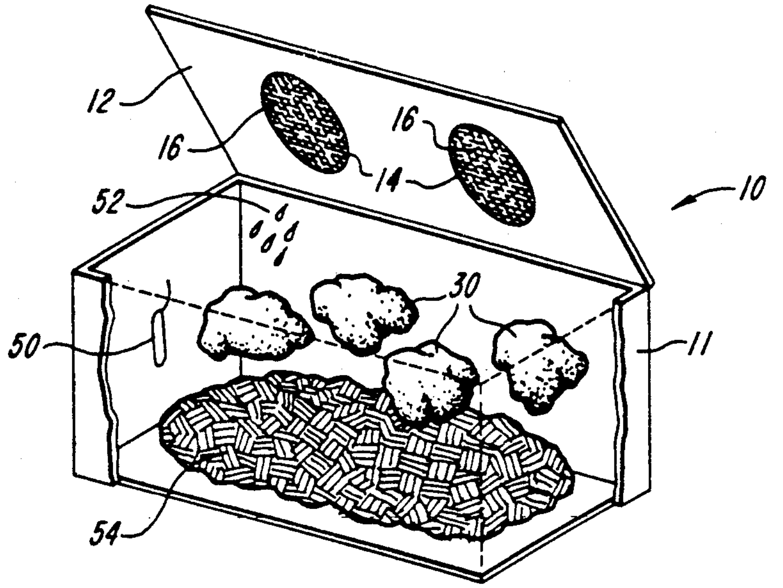
Figure 3:
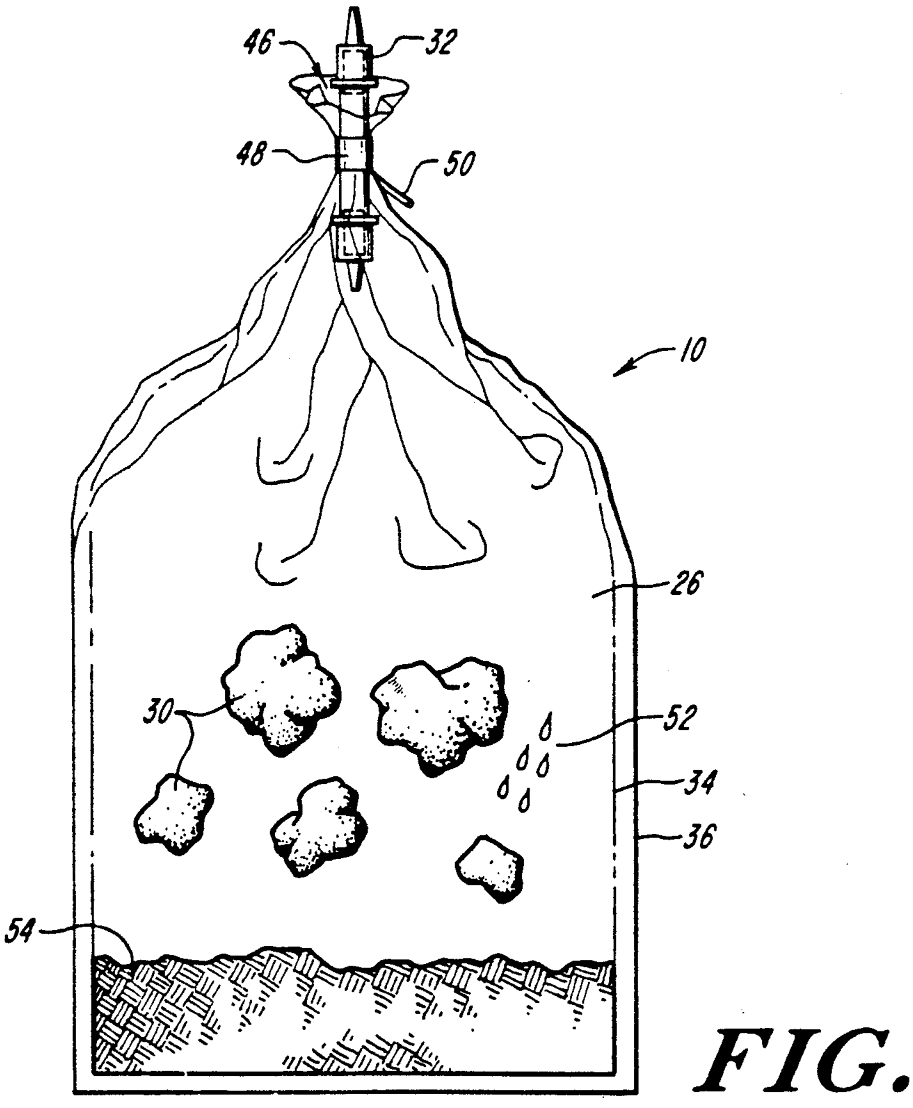

Referring to FIGS. 1 and 3, the apparatus 10 of the present invention may feature either a rigid or flexible container, preferably constructed of a nonporous transparent polymeric material. FIG. 1 illustrates one embodiment of the invention comprising a rigid container 11 having a removable lid 12 and one or more vent holes 14 disposed in the top surface of the lid. Seated within the vent holes are filter elements 16 which are removably and replaceably secured within the vent holes.

Where the apparatus 10 of the present invention consists of a rigid container 11, as shown in FIG. 1, it may be constructed of a nonporous, rigid polymer such as an acrylic or other suitable transparent or translucent polymer. The rigid container 11 may be of virtually any shape, however square and rectangular containers are preferred. Also, the size of the container may vary depending upon the applications for which it is desired. Typically, a rectangular rigid container has a preferred size of approximately 12×24×6 inches so as to be useful in conventional autoclaves.

Preferably, rigid container 11 features a lid 12 which may be either removable and replaceable or openable by way of hinge. In any event, the container 11 is designed such that when the lid 12 is in the closed position it may be securely sealed to prevent any exit of gas through the seam and the lid. The lid may have a natural (i.e., polymeric) hinge or a mechanical hinge and a locking element which ensures that the lid 12 may be maintained in a closed position. Alternatively, the lid may be slideably joined to and seated upon the main portion of the container 11.

The filter element 16 used in conjunction with rigid container 11 is preferably a cylindrical cartridge containing activated charcoal in particulate form. FIG. 2 illustrates one embodiment of a filter cartridge 16 useful with the present invention. As shown in FIG. 2, the filter has a housing 18 constructed of a material such as a metal or plastic. The housing 18 has a side wall and top and bottom surfaces. The side walls 20 of the housing are preferably solid while the top and bottom surfaces 22*a*, 22*b* of the housing are mesh-like, featuring a number of very small holes to allow the passage of gas therethrough. Preferably, the mesh size of the top and bottom surfaces 22*a*, 22*b* is between about 1/32 and 1/16 of an inch. In the illustrated embodiment, an absorbent material 24 such as activated charcoal, in powdered or granulated form, is disposed within the interior of filter 16.

The filter 16 may be operably disposed within the vent holes 14 of the rigid container 10 so that gases exit the container through the filter or filters. While exiting the container through filter 16, any radioactive compounds entrained within existing gases will be trapped within the absorbent filter material 24 of the filters. Accordingly, the gases exiting the container 10 and passing into the environment of the autoclave will be free of radioactivity.

FIGS. 3 and 4 illustrate another embodiment of the invention in which a flexible container 26 may be utilized. Such a flexible container 26 may be constructed of a polymeric film such as polypropylene. The flexible container 26 has at least one opening 28 disposed therein to enable waste materials 30 to be inserted within the container. An elongated filter element 32 may be disposed within the opening of the container in such a way that gas exits the container only by passing through the filter 32.

The flexible container 26, illustrated in FIG. 3, may be constructed of virtually any nonporous polymeric material able to withstand autoclaving temperatures. An example of a preferred material is polypropylene film having a thickness of approximately 0.04 mm–0.1 mm. In a preferred embodiment the flexible container may take the form of a polypropylene bag having a size of approximately 12×24" and a thickness of about 0.04 mm. The flexible container 26 can also be constructed of two such polypropylene bags, which are nested such that one is disposed within the other. The inner bag 34 may be used to house waste material 30 while the outer bag 36 is used as a safety precaution in the event that the inner bag ruptures. In an alternative embodiment, a single bag having sufficient strength and thickness (e.g., 0.08 to 0.10 mm) may be used.

An elongated filter element 32, illustrated in FIGS. 3 and 4, preferably is used in conjunction with the flexible container 26. As shown in FIG. 4, the filter 32 may be a hollow, elongate member having removable end caps 38. The end caps 38 may or may not be tapered. A central, cylindrical tube 40 of the filter 32 houses an activated charcoal material 42 which absorbs and retains radioactive materials. A small amount of glass wool, or similar material, 44 may be disposed at either end of tube 40, adjacent charcoal 42 and end caps 38 to help maintain the charcoal in place and provide further filtration and/or entrapment of particulates. Alternatively, a plastic screen or similar structure may be used to secure the charcoal in position.

A flow path through filter 32 is defined by the end caps 38 and the cylindrical tube 40. As noted above, activated charcoal 42 and glass wool 44 are preferably disposed within the flow path. Thus, when the filter is secured within an opening 46 in the flexible container 26, any gas exiting the bag passes through the filter 32. Radioactive compounds contained in the exiting gas are trapped within the charcoal and a radiation-free gas exits the filter 32.

The filter 32, illustrated in FIG. 4, may be secured within an opening 46 of the container 26 by virtually any suitably means. Preferably, the filter 32 is carefully placed within the opening such that a portion (e.g., approximately half) of the filter extends into the container while the other half of the filter extends out of the container. The filter 32 may then be securely sealed within the opening 46 by means of a heavy-duty elastic band 48 or other clamping material such as tape (e.g., autoclave tape) or a mechanical clasp. Filter 32 should be secured within an opening 46 in such a way that gas is only able to exit the bag through filter 32.

Although filter 32 is described as a cylindrical apparatus which is separate from container 26 and best suited for placement within the opening 46 of container 26, it should be understood that various alternative filter constructions may be utilized. For example, it may be advantageous to use a filter apparatus which is integrated with and disposed within the skin of container 26.

The container of the present invention, whether constructed of a flexible or a rigid material, should be used in conjunction with autoclaving indicators such as autoclave tape or Diack tubes. Such indicators are well known in the art and are designed so as to undergo a noticeable change in color of appearance upon being autoclaved under suitable conditions and upon reaching a predetermined temperature. Preferably, the controls should appear within the container where the solid waste materials 30 are disposed, and outside of the container as well. In this way, one will be assured that the interior as well as the exterior of the container have been subjected to suitable autoclaving conditions. As shown in FIGS. 1 and 3, Diack tubes or similar indicators 50 are affixed within container 11 and outside container 26. Although not shown in the drawings, any container used to store the waste materials should have at least one, and preferably two or more, autoclaving indicators disposed inside and outside of the container.

In the embodiments of both FIGS. 1 and 3, a small amount of water 52 or other moisture-laden material preferably is added to the container within which the solid waste 30 is housed. The term "moisture" is used herein to encompass water and other volatile liquids suitable for autoclaving. The addition of moisture to the container ensures that autoclaving will take place and thus provides an effective means of penetrating and inactivating biological contaminants of the waste materials 30. The amount of moisture to be added will, of course, vary depending upon the size of the container used as well as the size and mass of the waste materials within the container. Preferably, from 1 to 10 ml. of water may be used, and more preferably approximately 2-3 ml. of water may be used. Most preferably, the amount of water to be added is the minimum amount of water necessary to generate a positive autoclaving reading on the autoclaving indicators. Alternatively, other volatile liquids capable of distributing sufficient sensible heat to kill any microorganisms within the container can also be used. The desired amount may be determined by varying autoclave conditions and performing bacterial spore growth tests.

In addition to the water, an absorbent material 54 can be incorporated within the container to remove any moisture or other condensation from the interior of the container which may be generated during the autoclaving procedure. This is necessary to ensure that the container will be moisture free and suitable for disposal within a licensed radioactive solid waste disposal site. The amount of absorbent material 54 will, of course, vary depending on the amount of water added as well as the size of the container. Preferably, however, the amount of absorbent ranges from 4 to approximately 12 ounces by volume. One having ordinary skill in the art may easily determine the appropriate amount of absorbent material to be used in a given application. Absorbent materials useful in conjunction with this invention are well-known to those having ordinary skill in the art. One exemplary material is sold under the trademark SPEEDI-DRI by Englehard Corp, Specialty Chemical Division, of Edison, N.J. The absorbent may be added to the interior of the container in loose form, or may alternatively be contained within small packets which can be disposed within the container in desired locations, for example, or adhered to the container walls.

The present invention can be utilized by selecting the appropriate container for housing the solid waste materials. Solid waste materials which are both radioactively and biologically contaminated can then be disposed within the interior of the container. Also, a desired amount of water, for example, 2 ml., and approximately 6 ounces (by volume) of an absorbent material (e.g. SPEEDI-DRI) may be added to the interior of the container as well. The container should also feature ore or more Diack controls and/or several strips of autoclave tape disposed within the interior of the container, and at least on Diack control tube and several strips of autoclave tape affixed to the outside of the container. The filter is then securely sealed within the opening or openings of the container, and the container placed within an autoclave which is then activated. The conditions under which autoclaving should take place may vary depending upon the types of biological contaminants and the volume of waste material. These conditions may be determined by one having ordinary skill in the art. Preferably, however, the autoclaving will take place at approximately 121° C. under a pressure of approximately 30 psi for approximately 30 to 40 minutes. These conditions have been sufficient to inactivate most bacteria and viruses, including the HIV virus. Following the autoclave procedure, visual inspection of the container will reveal that the Diack controls and autoclave tape both on the inside and outside of the container will have undergone a visible change in appearance, thus indicating that the autoclaving conditions were sufficient.

Following the autoclaving procedure, the biological contaminants will have been fully inactivated, leaving a waste material which is only radioactive. The waste material, including the container and filter, may be handled and disposed of in a manner conventional for radioactive solid waste materials. For example, these materials may be disposed of at a radioactive solid waste landfill.

Although the present invention has been described with respect to currently preferred embodiments, those having ordinary skill in the art may make modifications and variations to the invention without exceeding the scope of the invention. For example, the design of filters and the filtering material useful with the embodiments of the invention may be altered. Various filter materials can be used in lieu of carbon or charcoal, including ceramic materials having absorbent materials incorporated into the porous channels in the ceramic matrix, or fibrous matrices, again incorporating absorbent materials. Additionally, the gases passing through the filter need not be vented into the autoclave environment but rather they can be trapped in another portion of the containment means or in an auxilliary container for disposal. Also, changes may be made to the method of seating the filter or filters within the waste container, again without exceeding the scope of the present invention.

What is claimed is:

1. An apparatus for housing solid, radioactively and biologically contaminated waste during steam autoclave treatment thereof, comprising:

a container means for housing solid radioactive biological wastes, suitable for use during an autoclaving procedure, having at least one opening therein;

a filter means for entrapping radioactive compounds contained in gases exiting said container means during autoclave treatment, said filter means being securely disposed within an opening of the container means such that any gas exiting the container means during autoclave treatment passes through the filter means; and indicator means for establishing that the biologically contaminated waste has been inactivated by exposure to a predetermined autoclaving temperature.

2. The apparatus of claim 1, wherein the filter means comprises a cartridge having a flow path therethrough with a filter material disposed in the flow path.

3. The apparatus of claim 2 wherein the filter material comprises activated charcoal.

4. The apparatus of claim 1, wherein the container means comprises a rigid structure made of a nonporous thermally resistant material.

5. The apparatus of claim 4, wherein the container means is constructed of an acrylic material.

6. The apparatus of claim 1, wherein the container means comprises a nonporous polymeric autoclaving bag.

7. The apparatus of claim 1, wherein the container means comprises a nonporous polymeric autoclaving bag nested within a similarly constructed autoclaving bag.

8. The apparatus of claim 1, wherein the filter means is disposed within the opening of the container means.

9. An apparatus for housing solid radioactively and biologically contaminated waste during steam autoclave treatment thereof, comprising:

a container means for housing solid radioactive biological wastes, suitable for use during an autoclaving procedure, having at least one sealable opening therein and at least one filter-retaining opening therein;

a filter means for entrapping radioactive compounds contained in gases exiting said container means during autoclave treatment, said filter means being securely disposed within the filter-retaining opening of the container means such that any gas exiting the container means during autoclave treatment passes through the filter means; and indicator means for establishing that the biologically contaminated waste has been inactivated by exposure to a predetermined autoclaving temperature.

* * * * *